United States Patent [19]
Carminucci

[11] Patent Number: 5,938,693
[45] Date of Patent: Aug. 17, 1999

[54] MOIST HEAT IN VAPOR FORM HEALTH AND BEAUTY THERAPEUTIC SYSTEM

[75] Inventor: Robert N. Carminucci, East Chatham, N.Y.

[73] Assignee: Philips Electronics North America Corporation, New York, N.Y.

[21] Appl. No.: 08/498,287

[22] Filed: Jun. 30, 1995

[51] Int. Cl.⁶ .................................................. A61F 7/00
[52] U.S. Cl. .................... 607/104; 607/108; 607/109; 607/112; 607/114
[58] Field of Search ................. 607/96, 99, 104, 607/108–112, 84, 83

[56] References Cited

U.S. PATENT DOCUMENTS

| | | | |
|---|---|---|---|
| 3,152,240 | 10/1964 | Scott | 607/84 X |
| 3,351,737 | 11/1967 | Katzman et al. | 607/84 X |
| 3,463,160 | 8/1969 | Halonen | 607/84 |
| 3,493,722 | 2/1970 | Popeil | 607/84 X |
| 3,511,236 | 5/1970 | Conlin et al. | 607/84 X |
| 3,707,971 | 1/1973 | Yamamoto | 607/84 |
| 3,712,307 | 1/1973 | McLaughlin | 607/84 |
| 3,749,092 | 7/1973 | Williams | 607/84 X |
| 3,768,483 | 10/1973 | Kusunoki | 607/84 |
| 3,949,743 | 4/1976 | Shanbrom | 607/84 X |
| 4,106,477 | 8/1978 | Feld | 126/263 |
| 4,314,138 | 2/1982 | Itoh | 219/276 |
| 4,597,917 | 7/1986 | Lunsford | 261/153 |
| 4,616,122 | 10/1986 | Burian | 607/84 |
| 4,621,641 | 11/1986 | Frank et al. | 607/84 |
| 4,736,088 | 4/1988 | Bart | 219/211 |
| 4,844,072 | 7/1989 | French et al. | 128/400 |
| 4,891,501 | 1/1990 | Lipton | 219/527 |
| 5,097,828 | 3/1992 | Deutsch | 128/399 |
| 5,179,944 | 1/1993 | Mcsymytz | 128/403 |
| 5,181,510 | 1/1993 | Peters | 607/109 |
| 5,246,697 | 9/1993 | Conte et al. | 424/78.03 |
| 5,292,347 | 3/1994 | Pompei | 607/104 |
| 5,545,196 | 8/1996 | Falk | 607/104 X |

FOREIGN PATENT DOCUMENTS

| | | | |
|---|---|---|---|
| 2051196 | 7/1992 | Canada | A61F 7/08 |
| 1109173 | 8/1984 | U.S.S.R. | A61M 17/00 |

OTHER PUBLICATIONS

Herbal Steam Facial.., Health Center for Better Living, Inc. p. 62, 1994 Catalog.
Passport by Invacare, Owner's Manual, Form No. 91–211, Rev. H. Apr. 1994, pp. 1–15.
Inhale Your Medicine, 86/Design News/6–13–94.
What's New About the Pulmo–Aide?, 1994 DHC. Inc. LT–1435 REFV. D.

*Primary Examiner*—Robert L. Nasser
*Attorney, Agent, or Firm*—Ernestine C. Bartlett

[57] ABSTRACT

A therapeutic system comprises a generator for generating moist heat in vapor form. The generator comprises a housing having a vapor chamber and a fluid reservoir, the fluid reservoir for receiving a fluid to be vaporized. The housing further contains a heater for heating the fluid received in the fluid reservoir in a first controlled manner to produce the moist heat in vapor form, wherein the moist heat in vapor form produced is contained in the vapor chamber. An interface remote from the generator interfaces the moist heat in vapor form with a desired treatment area. A delivery mechanism connected between the generator and the interface delivers the moist heat in vapor form from the generator to the interface in a second controlled manner. Lastly, a controller connected with the generator and the delivery mechanism controls the heating of the fluid received in the fluid reservoir in the first controlled manner and further controls the delivery of moist heat in vapor form to the treatment area in the second manner. The generator further provides for the inclusion of a treatment additive to the moist heat in vapor form.

15 Claims, 4 Drawing Sheets

MOIST HEAT IN VAPOR FORM HEALTH AND BEAUTY THERAPEUTIC SYSTEM

BACKGROUND OF THE INVENTION

1. Field of the Invention

This invention generally relates to a thermal therapy system for providing moist heat, and more particularly, to a thermal therapy system for providing moist heat in vapor form to a desired treatment area of a patient.

2. Discussion of the Related Art

Therapeutic treatment of a patient's skin can vary widely, to include such treatments as treatments for cleansing, treatments for preparation, conditioning, exfoliation and feeding, and burn treatment. Therapeutic treatments may also include premature infant treatment, pre-treatment for physiotherapy, and treatment of muscle and joint injuries.

The use of heat and cold for therapeutic purposes is well known. With respect to heat treatments, a majority of therapeutic systems and devices simply provide for the application of dry heat or moist heat. For instance, in U.S. Pat. No. 4,844,072 a liquid-circulating thermal therapy system is disclosed in which the liquid-circulating thermal therapy system circulates hot or cold liquid through a pad placed in thermal contact with the patient undergoing thermal therapy. The system includes a flexible thermal pad with an internal channel for carrying the liquid and a pump assembly for circulating and optionally heating the liquid. The patient-contacting surface of the pad comprises foam having a cushioned surface, further in which the foam comprises an open-cell foam structure for absorbing and retaining moisture for applying moist heat. One drawback of the '072 system is its inability to provide "moist heat in vapor form" for treatment of a desired area. In addition, the '072 system is not readily adaptable for introducing treatment additives to a moist heat in vapor form for altering a treatment as may be required for a particular type of treatment.

Another heat treatment device is disclosed in U.S. Pat. No. 5,097,828. The '828 device includes a handle, a thermally conductive head secured to the handle, and a heating/cooling device inside the thermally conductive head. A bag filled with a thermally conductive fluid is mounted to the head for conforming to the surface of the body to which it is applied. Furthermore, a porous bag is employed if moist heat is desired. Similar as indicated above with respect to the '072 system, the '828 device lacks an ability to provide "moist heat in vapor form" for treatment of a desired area, and further is not readily adaptable for introducing treatment additives to a moist heat in vapor form for altering a treatment as may be required for a particular type of treatment.

Yet another treatment device includes an herbal steam facial device, such as is commercially available from KAZ, Inc., 41 Cross Street, Hudson N.Y. The herbal steam facial device principally comprises a vapor generator having a fixed molded housing for facial exposure to a heated vapor. While the herbal steam facial device provides a heated vapor, such a device is not well suited for a multiplicity of treatment applications.

SUMMARY OF THE INVENTION

An object of the present invention is to overcome the problems in the art discussed above.

Another object of the present invention is to provide a moist heat in vapor form therapeutic system having an ability to deliver and apply moist heat in vapor form to any area of a patient's body requiring treatment.

Yet another object of the present invention is to provide a system capable of advantageously controlling temperature, quantity of vapor delivered, and a duration of moist heat in vapor.

According to the present invention, a therapeutic system for applying a moist heat in vapor form to a desired treatment area requiring therapeutic treatment comprises a means for generating a moist heat in vapor form. The moist heat in vapor form generator comprises a housing having a vapor chamber and a fluid reservoir, the fluid reservoir receiving a fluid to be vaporized. The housing further includes a means for heating the fluid received in the fluid reservoir in a first controlled manner to produce moist heat in vapor form, wherein the moist heat in vapor form thus produced is contained in the vapor chamber. The generator further comprises a vapor output port. An interface means, remote from the generator, interfaces the moist heat in vapor form with the desired treatment area. A delivery means is connected between the generator and the interface means for delivering the moist heat in vapor form from the generator to the interface means in a second controlled manner. Lastly, a control means connected with the generator and the delivery means controls the heating of the fluid received in the fluid reservoir in the first controlled manner and further controls the delivery of moist heat in vapor form to the treatment area in the second manner.

BRIEF DESCRIPTION OF THE DRAWINGS

The foregoing and other teachings and advantages of the present invention will become more apparent upon a detailed description of the best mode for carrying out the invention as rendered below. In the description to follow, reference will be made to the accompanying drawings in which like reference numerals are carried forward, and in which.

DETAILED DESCRIPTION OF THE PREFERRED EMBODIMENTS

Figure 1:
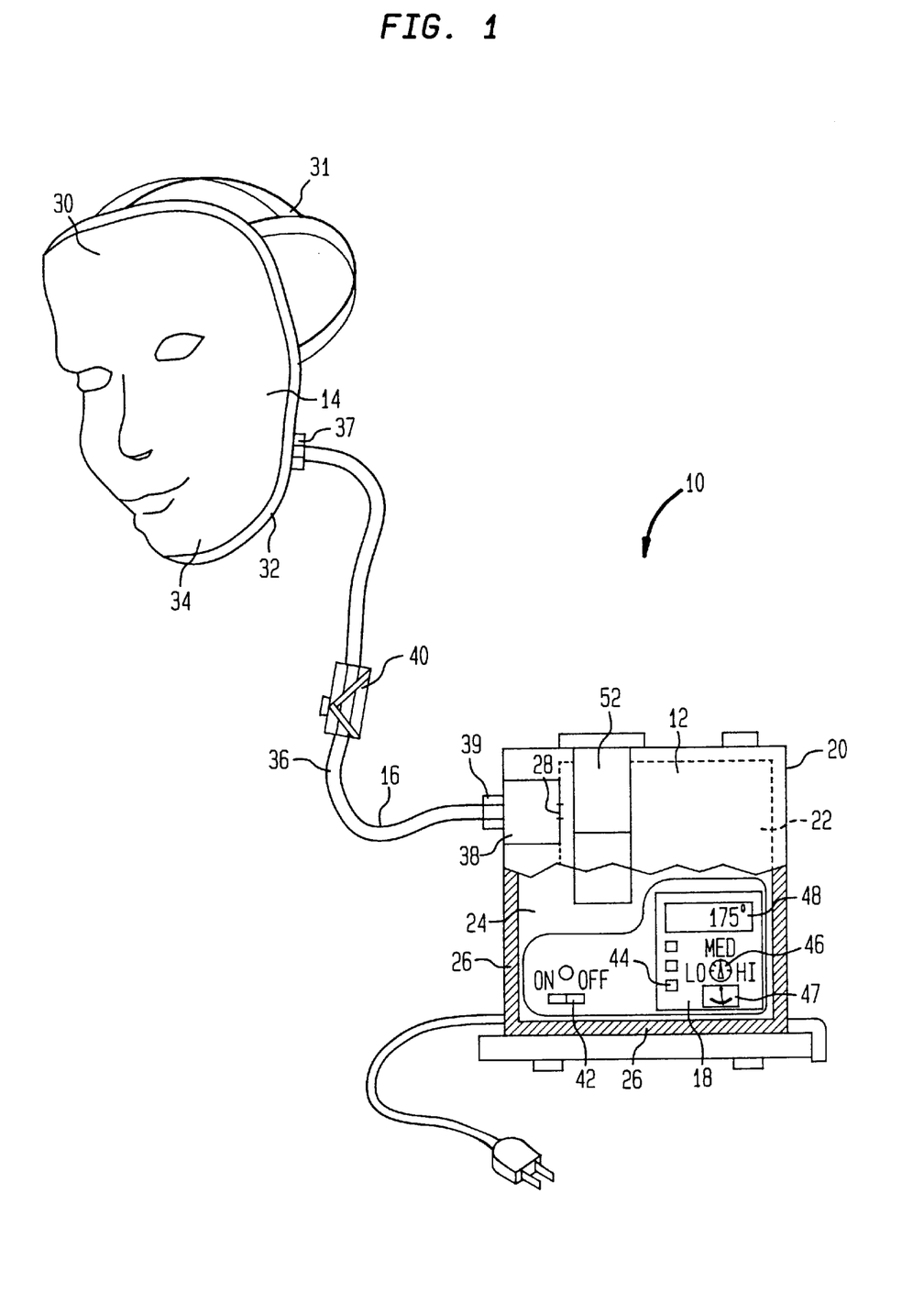
FIG. 1 shows a plan view of the moist heat in vapor form therapeutic system according to the present invention.

Referring now to FIG. 1, there is shown a therapeutic system 10 for applying a moist heat in vapor form to a desired treatment area requiring therapeutic treatment. The therapeutic system 10 comprises a means 12 for generating a moist heat in vapor form, an interface means 14 remote from said generating means 12 for interfacing the moist heat in vapor form with the desired treatment area, a delivery means 16 connected between said generating means 12 and said interface means 14 for delivering the moist heat in vapor form from the generating means 12 to the interface means 14, and a controller 18 connected with the generating means 12 and the delivery means 16 for controlling the generating means 12 and further for controlling the delivery of moist heat in vapor form to the treatment area.

Generating means 12 comprises a housing 20 having a vapor chamber 22 and a fluid reservoir 24, the fluid reservoir 24 for receiving a fluid, such a water or other suitable liquid for a desired treatment, to be vaporized. In one embodiment of the invention, the vapor chamber and the fluid chamber constitute a single chamber, wherein the fluid is contained in the lower portion of the chamber and the vapor is contained in the upper portion of the chamber. The vapor chamber is of sufficient volume to contain enough moist heat in vapor form so as to provide for a continuous supply of moist heat in vapor form, as necessary, for the requirements of a particular treatment application. Housing 20 further comprises a controllable heater 26. Heater 26 can comprise any suitable controllable heating element. Heater 26 is placed in proximity to the fluid reservoir 24 for heating the fluid received in the fluid reservoir in a first controlled manner to nebulize and produce moist heat in vapor form. Nebulization consists of the reducing of a liquid into a fine spray or mist. Nebulization is known in the art and thus only briefly discussed herein. Moist heat in vapor form produced as a result of the nebulization of the fluid in the fluid reservoir 24 is thereafter contained in the vapor chamber 22. A suitable pressure relief valve or other form of venting (not shown) can be utilized to prevent any adverse pressure build up within the vapor chamber. Generating means 12 further comprises a vapor output port 28 though which moist heat in vapor form exits from the vapor chamber 22.

Interface means 14 is positioned remote from generating means 12 for interfacing the moist heat in vapor form with a desired treatment area, such as a patient's face. As shown in FIG. 1, interface means 14 comprises a mask 30, and more particularly, a facial mask. The facial mask may be manufactured in suitable sizes as appropriate for a range of patients. Interface means 14 further includes suitable straps and/or fasteners 31 for attachment of the same to the desired treatment area of the patient under treatment. Interface means 14 preferably comprises an inner liner 32 and an outer liner 34, wherein the inner liner 32 comprises a breathable fabric of a first permeability for allowing the moist heat in vapor form therethrough and further for placement in proximity to the desired treatment area. The breathable fabric of liner 32 can comprise any suitable breathable fabric for passing vapor therethrough, such as, a micro-porous membrane. The inner liner may further comprise a single use type liner or it may likewise comprise a reusable liner, taking into consideration that a reusable liner would require appropriate cleaning between uses. The outer liner 34 is of a second permeability that is less than than the first permeability, wherein moist heat in vapor form exits through the outer liner 34 at a greatly reduced rate or is prevented completely from passing though the outer liner 34, depending upon the permeability thereof. Liner 34 comprises any suitable material having the desired permeability. In either instant, the permeability of the outer liner 34 is less than that of the inner liner 32. The external surface of the mask 30 can comprise outer liner 34, wherein the outer liner 34 has a shape in conformity with the desired treatment area. In accordance with the present invention, flow of moist heat in vapor form is through the inner liner 32 to thereby expose the desired treatment area to the moist heat in vapor form.

Delivery means 16 comprises flexible tubing 36 and pump 38 connected between the generating means 12 and the interface means 14 for delivering the moist heat in vapor form from the generating means 12 to the interface means 14 in a second controlled manner. Tubing 36 is fastened to interface 14 at one end thereof via any suitable connection means 37, such as, commercially available tubular quick-connect connector. An opposite end of tubing 36 is similarly connected via a suitable connection means 39 to pump 38. Pump 38 comprises any suitable pump, such as, a controllable bellows type pump. Pump 38 is connected with vapor chamber 22 at the vapor output port 28 for pumping moist heat in vapor form from the chamber 22 via tubing 36 to the remote interface means 14 to effectively transport the moist heat in vapor form to the desired treatment area of the patient undergoing treatment. In one embodiment, tubing 36 comprises a single tube, for use in delivering moist heat in vapor form to the interface means 14. In an alternate embodiment, tubing 36 comprises a first flexible tube and a second flexible tube, the first tube being used for delivering moist heat in vapor form to the interface means 14 and the second tube being used for recapturing or exhausting the moist heat in vapor form away from the interface means 14, as will be explained further herein below. In addition, a flow regulator or valve 40, such as a pinch valve or other suitable controllable valve, may be used in conjunction with the tubing 36 and pump 38 for providing a desired regulation of the flow of moist heat in vapor form through delivery means 16. While flow valve 40 is shown to be positioned intermediate tubing 36, it may likewise be positioned proximate to pump 38, as best suited for the particular requirements of a treatment application.

Figure 2:
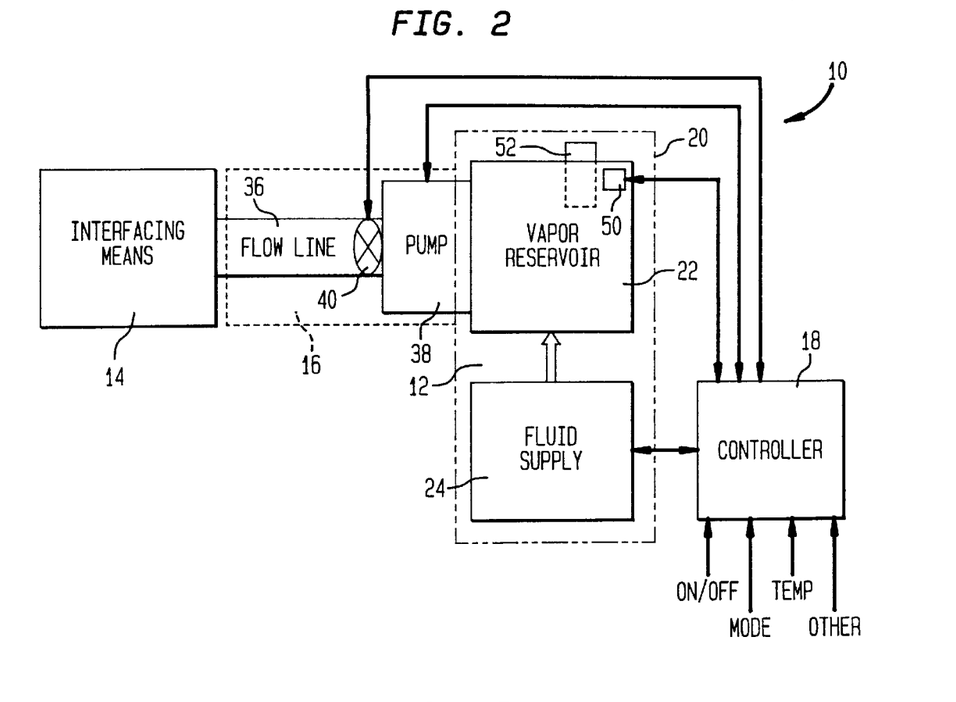
FIG. 2 shows a block diagram representation of the moist heat in vapor form therapeutic system according to the present invention.

Referring now to FIGS. 1 and 2, control means 18 is connected with the generating means 12 and the delivery means 16 for controlling the heating of the fluid received in the fluid reservoir 24 in the first controlled manner and further for controlling the delivery of moist heat in vapor form stored in the vapor chamber 22 to the treatment area in the second manner. Control means 18 comprises, for example, a microcomputer or the like, to include interface circuitry as necessary, for receiving certain input information signals, the microcomputer being programmed by known techniques for performing the desired functions as will be described herein below. Controller 18 may likewise comprise discrete circuitry for performing the desired functions.

Control means 18 can receive signal inputs from such devices as an ON/OFF power switch 42, a mode selection switch 44, a temperature setting switch 46, and any other switch, such as a time setting switch 47, as may be appropriate for incorporation into the device 10 pursuant to a particular treatment application (see FIG. 1). Controller 18 may also include a display 48 for displaying pertinent information, such as, the temperature of the moist heat in vapor form, for observation by a device user.

In addition to the aforesaid inputs, controller 18 receives further inputs. For instance, a suitable temperature/pressure sensor is positioned by suitable means within the vapor chamber, to thereby provide a means for monitoring a temperature of the moist heat in vapor form. As indicated above, heater 26 comprises a controllable heater and controller 18, being responsive to a temperature setting input signal and an input signal from the temperature/pressure sensor 50, provides an appropriate control signal to heater 26 for controlling the same. Controller 18 further provides an appropriate control output to pump 38 of delivery means 16. In this manner, controller 18 can provide the appropriate control signal for regulating pump 38 on/off and, in addition, for controlling a rate of pumping of the moist heat in vapor form by pump 38. In an instance where valve 40 comprises a controllable valve (FIG. 2), controller 18 can further provide an appropriate control signal for regulating the valve and providing a desired flow restriction as may be necessary for the particular requirements of a treatment application.

Referring once again to FIG. 1, moist heat in vapor form generator 18 of device 10 further comprises a means 52 for providing a treatment additive to the moist heat in vapor form. In a first embodiment of the invention, the treatment additive providing means 52 comprises a suitable receptacle or container positioned within the vapor reservoir by suitable securing means, for receiving and containing a treatment additive. In this first embodiment, the treatment additive is directly exposed to the moist heat in vapor form, wherein treatment additive is effectively absorbed therein. The treatment additive may be in liquid or gel form. Treatment additive providing means 52 may likewise comprise any suitable controllable dispenser. Alternatively, the treatment additive providing means 52 may be positioned within the fluid reservoir for providing a treatment additive directly to the fluid to be vaporized, wherein the treatment additive can thereby be incorporated into the moist heat in vapor form. Treatment additive may be in liquid, gel, and/or tablet form for use with this later embodiment. Treatment additive means 52 may also provide for an appropriate mixing of more that one additive at a same time. For instance, means 52 may comprise two or more compartments, each compartment for containing a desired treatment additive. The compartments could include output ports thereof for a metering of their contents into a common compartment, wherein the contents of the common compartment thereafter being exposed to the moist heat in vapor form for incorporation therein or being dispensed directly into the fluid reservoir for incorporation into the fluid to be vaporized.

In operation, the device according to the present invention produces moist heat in vapor form, delivers the moist heat in vapor form to the interface means 14, i.e., mask 30, and thereupon applies the moist heat in vapor form to the desired treatment area. The device user would place the mask 30 over his or her face during treatment. The mask would be held in place via the support straps 31. The user of the device also has the capability to completely control the temperature and quantity of vapor, in addition, to the duration of the treatment application. Any number of modes of operation can be programmed into the controller 18 for use in a variety of treatment applications. For instance, a particular mode of operation may specify a duration of treatment time, treatment temperature, rate of delivery of the moist heat in vapor form, and a duty cycle for the treatment. Other modes of operation are also possible. Furthermore, treatment additives suitable for a particular treatment application can be easily provided to the moist heat in vapor form. A mode of operation may also include the metered addition of treatment additives into the moist heat in vapor form as may be necessary for a particular treatment.

Potential treatment applications may include such treatments as facial treatments, for instance. One type of facial treatment can be directed towards the treatment of acne, in which, a suitable treatment additive is used. Another type of facial treatment includes preparation, conditioning, exfoliation, and feeding of the skin. This later type of facial treatment is especially useful in the areas of beauty and cosmetology. Likewise, a suitable additive for each of preparation, conditioning, exfoliation, and the feeding of the skin may be conveniently used in such a facial treatment with the device of the present invention. For instance, a concentrated additive of an herbal remedy may be placed into the treatment additive means 52 for adding such an herbal remedy to the moist heat in vapor form for the desired treatment. Such herbal additives may include teatree oil, calendula flower, echinacea root, pennyroyal, spearmint, elder flower, lavender, sage, and chamomile. Another such additive may include alpha-hydroxy acid, which is used as a skin preparation. Alpha-hydroxide, alpha-hydroxy acid, and its various derivatives act as an exfoliate and may be used prior to an application of a conditioning additive. With the device of the present invention, a treatment can be tailored as necessary.

Figure 3:
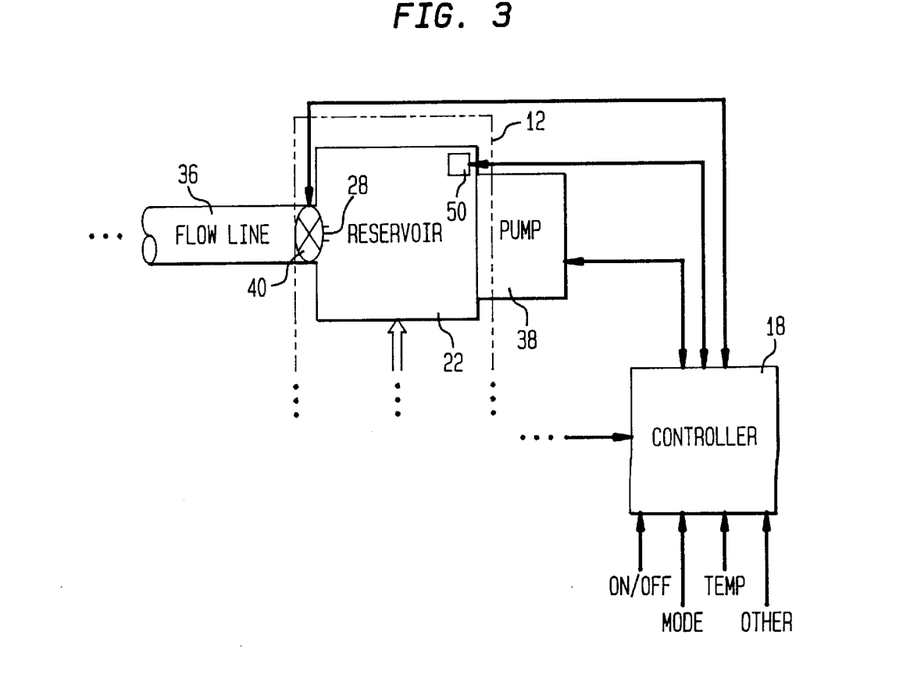
FIG. 3 shows a partial block diagram representation of an alternate embodiment of the present invention.

Referring now to FIG. 3, an alternate embodiment in accordance with the present invention is shown. The alternate embodiment is similar to the initial embodiment, with the following differences. Delivery means 16 comprises pump 38 in connection with the vapor chamber 22 of the generating means 12 for pumping moist heat in vapor form from the vapor chamber 22 through the vapor output port 28. In this embodiment, delivery means 16 further comprises a flexible tubing 36 connected between the vapor output port 28 and the interface means 14 for transporting pumped moist heat in vapor form to the interface means 14. In addition, valve 40 is positioned proximate vapor output port 28 for providing flow control as appropriate.

Figure 4:
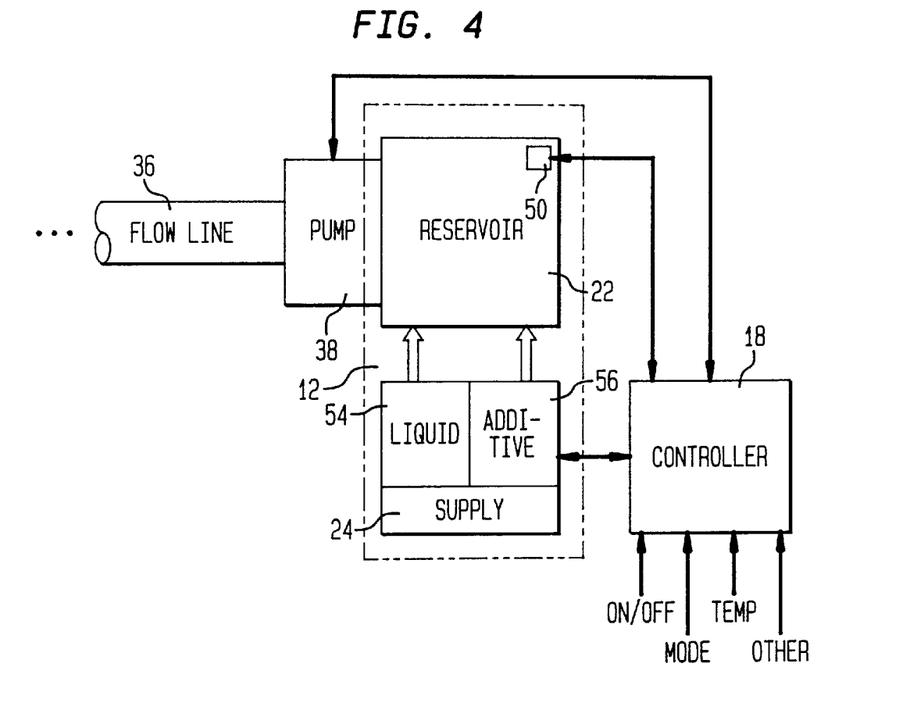
FIG. 4 shows a partial block diagram representation of another alternate embodiment of the present invention.

Referring now to FIG. 4, another alternate embodiment in accordance with the present invention are shown. The alternate embodiment is similar to the initial embodiment, with the following differences. Fluid supply or reservoir 24 further comprises first and second compartments 54 and 56. Compartment 54 is for containing the principal liquid for nebulization and vaporization. Compartment 56 is for containing a liquid having a treatment additive therein for nebulization and vaporization, separate from that of the liquid contained in compartment 54. In other words, the contents of each compartment are heated and nebulized separate from one another. Heater 26 would comprise first and second heaters, one each for use with the first and second compartments 54 and 56, respectively. Respective outputs of each compartment are fed into vapor reservoir 22, wherein a composite mixture of moist in heat vapor form is created. This composite mixture of moist heat in vapor form is transported by delivery means 16 to interface means 14 similarly as with that of the initial embodiment.

Figure 5:
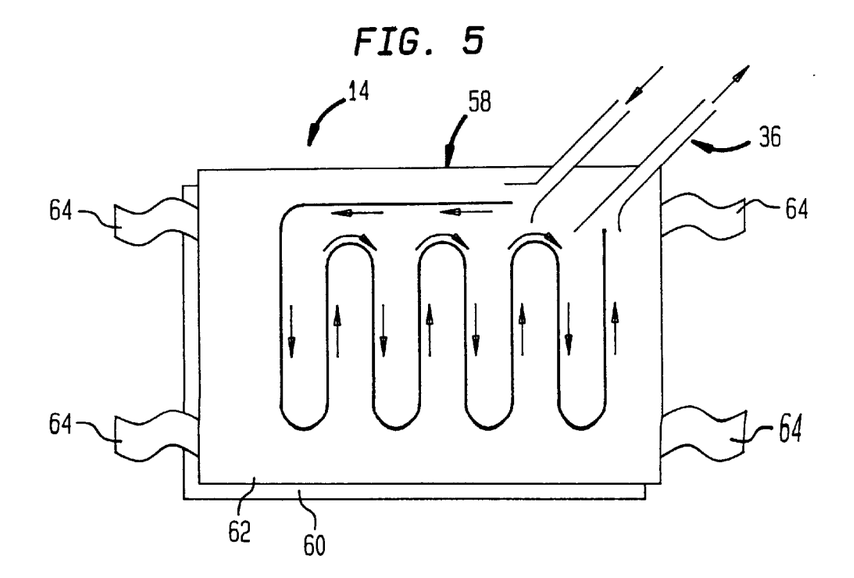
FIG. 5 shows a pad according to yet another alternate embodiment of the present invention.

Turning now to FIG. 5, interface means 14 may further comprise a pad 58. Pad 58 preferably comprises an inner liner 60, an outer liner 62, and suitable straps 64 for securing pad 58 about a desired area for treatment. Inner liner 60 is for placement in intimate contact with the desired treatment area. Inner liner 60 may also have suitable channels therein for directing a flow of moist heat in vapor form as necessary therein, for instance, as is shown by the arrows in FIG.5. Liners 60 and 62 are similar in composition to liners 32 and 34, respectively, of mask 30. Flow of moist heat in vapor form may flow into the pad via tubing 36 in the instance of having only one tube in the delivery means 16, or it may flow both into and out of pad 58 in the instance of having a supply tube and a return (exhaust) tube in the delivery means 16, as may be required for the particular treatment application.

Figure 6:
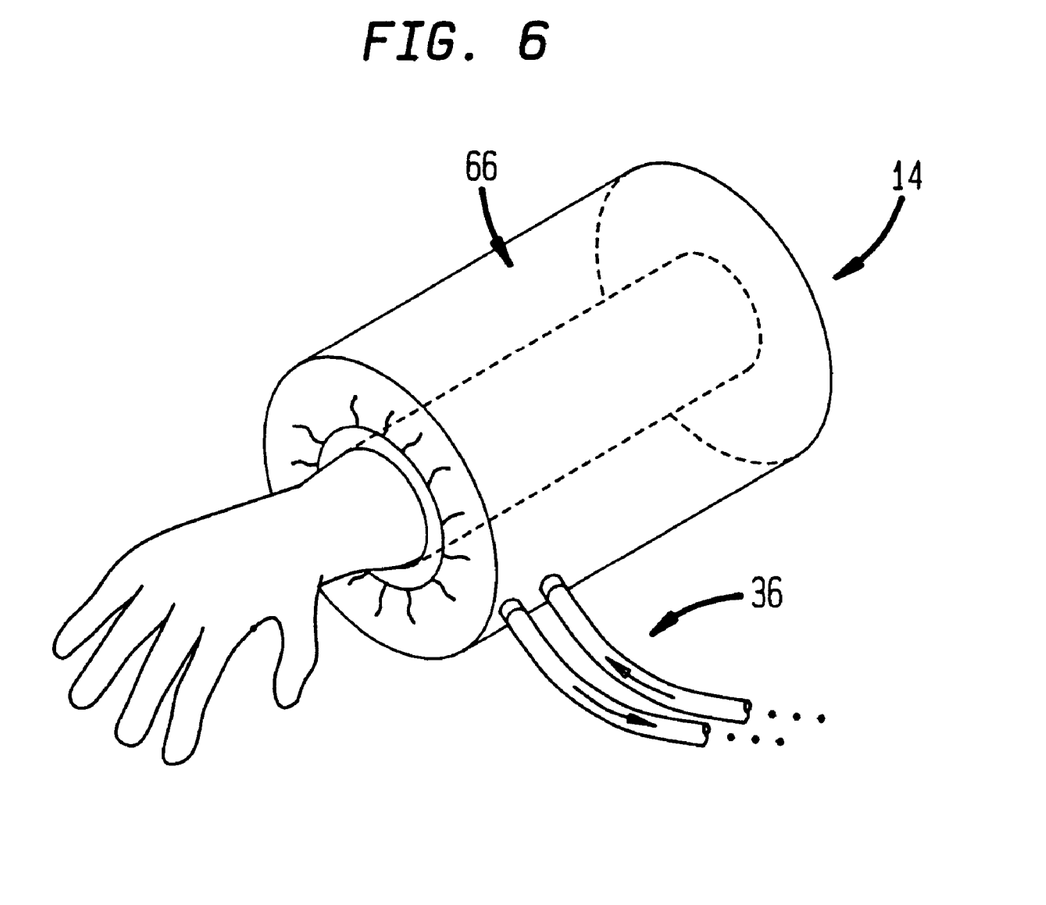
FIG. 6 shows a tent according to yet another alternate embodiment of the present invention.

Turning now to FIG. 6, interface means 14 may further comprise a tent 66, wherein the tent 66 comprises an inner liner 68 and an outer liner 70. Liners 68 and 70 are similar in composition to liners 32 and 34, respectively, of mask 30. The tent 66 provides a controlled atmosphere of the moist heat in vapor form around the desired treatment area, such as a user's arm. Flow of moist heat in vapor form may flow into the tent 66 via tubing 36 in the instance of having only one tube in the delivery means 16, or it may flow both into and out of the tent 66 in the instance of having a supply tube and a return (exhaust) tube in the delivery means 16, as may be required for the particular treatment application.

In the instances wherein a supply tube and a return tube are provided in the delivery means, delivery means 16 comprises pump 38 in connection with the vapor chamber 22 of the generating means 12 for pumping moist heat in vapor form from the vapor chamber 22 through the vapor output port 28. The delivery means 16 further comprises a first flexible tubing and a second flexible tubing, the first flexible tubing being connected between the vapor output port 28 and interface means 14 for transporting pumped moist heat in vapor form to the interface means 14. The second flexible tubing is connected between the interface means 14 and the pump 38 for recirculating or exhausting, as appropriate, the moist heat in vapor form from the interface means 14. In the case of recirculation of the moist heat in vapor form, such recirculation provides for the conservation of treatment additive, that is, use of the treatment additive is maximized.

In addition to the facial treatment discussed herein above, another treatment for which the present invention may be used is burn treatment. In this regard, the present invention may be used for the delivery and application of suitable treatment additives in vapor form to a burn area requiring treatment. Treatment additives, for this instance, may include antibiotics, coagulants, and healing components. Yet another treatment may include the creation of a simulated embryonic environment as an enhancement to traditional "isolette" units used in hospitals. The present invention is further applicable for use in treatment of bed-ridden patients, wherein one mode of operation of the present invention may be programmed for delivering three to five minute cycles every hour for treatment of bed sores with anti-irritants, or to promote circulation, and/or to deliver topical treatments. The present invention may also be applicable for treatment for arthritis pain reduction, pre- treatment prior to physical manipulation in physiotherapy, and assisting in the treatment of muscle and joint injuries. The present invention is thus highly adaptable for a multitude of treatment applications.

The present invention advantageously provides a high volume capacity for enabling extended, pleasant, and highly effective treatment periods. A user is allowed a certain degree of mobility due to the remote location of the interface means 14 from the generating means 12. Moist heat in vapor form may be dissipated through the breathable fabric bladder totally (via the supply tube only) or any excess residual moist heat in vapor form can be recirculated back to the vapor chamber 22 via a return line (via the supply and return tubes). In this latter instance, conservation of modified vapor manifests itself in longer, more economical treatment periods without interruption. The present invention advantageously provides a unit which incorporates heating, vaporizing, pumping, delivery, recirculation, modification with additives, temperature, flow control, and composition of modified moist heat in vapor form all in one source. Furthermore, the interface means takes various forms thus advantageously allowing greater flexibility for use in delivery of moist heat in vapor form to all areas to be treated.

While the invention has been particularly shown and described with reference to the preferred embodiment thereof, it will be understood by those skilled in the art that various changes in form and detail may be made therein without departing from the spirit and scope of the invention.

What is claimed is:

1. A therapeutic system for applying a moist heat in vapor form to a desired treatment area requiring therapeutic treatment, said system comprising:

means for generating a moist heat in vapor form, said generating means comprising a housing having a vapor chamber, a vapor output port, and a fluid reservoir for receiving a fluid to be vaporized, the housing further having means for heating the fluid received in the fluid reservoir in a first controlled manner to produce moist heat in vapor form, the moist heat in vapor form produced being contained in the vapor chamber;

interface means remote from said generating means for interfacing the moist heat in vapor form with the desired treatment area, wherein said interface means comprises an inner liner and an outer liner, wherein the inner liner comprises a breathable fabric of a first permeability for allowing the moist heat in vapor form therethrough and further for placement in proximity to the desired treatment area, and wherein the outer liner is of a second permeability that is less than the first permeability, whereby the desired treatment area is exposed to the moist heat in vapor form;

delivery means connected between and extending a predetermined distance from said generating means and said remote interface means for delivering the moist heat in vapor form from said generating means to said interface means in a second controlled manner, and control means connected with said generating means and said delivery means for controlling the heating of the fluid received in the fluid reservoir in the first controlled manner and further for controlling the delivery of moist heat in vapor form to the treatment area in the second manner,.

said interfacing, delivery and control means being associatively adapted to selectively apply moist heat in vapor form to any external body part for which treatment is desired.

2. The therapeutic system of claim 1, wherein said interface means further comprises a mask, wherein the mask comprises the inner liner and the outer liner, the mask having a shape in conformity with the desired treatment area.

3. The therapeutic system of claim 1, wherein said interface means further comprises a pad, wherein the pad comprises the inner liner and the outer liner, wherein the inner liner is for placement in intimate contact with the desired treatment area.

4. The therapeutic system of claim 1, wherein said interface means further comprises a tent, wherein the tent comprises the inner liner and the outer liner, the tent providing a controlled atmosphere of the moist heat in vapor form around the desired treatment area.

5. The therapeutic system of claim 1, wherein said interface means comprises an inner liner and an outer liner, wherein the inner liner comprises a breathable fabric of a first permeability for allowing the moist heat in vapor form therethrough and further for placement in proximity to the desired treatment area, and wherein the outer liner is of a second permeability that is less than the first permeability to effectively prevent the moist heat in vapor form from escaping therethrough, whereby the desired treatment area is exposed to the moist heat in vapor form.

6. A therapeutic system for applying a moist heat in vapor form to a desired treatment area requiring therapeutic treatment, said system comprising:

means for generating a moist heat in vapor form, said generating means comprising a housing having a vapor chamber and a fluid reservoir, the fluid reservoir receiving a fluid to be vaporized, the housing further having means for heating the fluid received in the fluid reservoir in a first controlled manner to produce moist heat in vapor form, the moist heat in vapor form produced being contained in the vapor chamber, said generating means further comprising a vapor output port and means for providing a treatment additive to the moist heat in vapor form;

interface means remote from said generating means for interfacing the moist heat in vapor form with the desired treatment area, said interface means comprising an inner liner and an outer liner, wherein the inner liner comprises a breathable fabric of a first permeability for allowing the moist heat in vapor form therethrough and further for placement in proximity to the desired treatment area, and wherein the outer liner is of a second permeability that is less than the first permeability, whereby the desired treatment area is exposed to the moist heat in vapor form;

delivery means connected between said generating means and said interface means for delivery the moist heat in vapor form from said generating means to said interface means in a second controlled manner wherein said delivery means comprises a pump connected to the vapor chamber of said generating means for pumping moist heat in vapor form from the vapor chamber through the vapor output port, and wherein said delivery means further comprises a flexible tubing connected between the vapor output port and said interface means for transporting pumped moist heat in vapor form to said interface means; and control means connected with said generating means and said delivery means for controlling the heating of the fluid received in the fluid reservoir in the first controlled manner and further for controlling the delivery of moist heat in vapor form to the treatment area in the second manner, said interfacing, delivery and control means being associatively adapted to selectively apply moist heat in vapor form to one or more body part selected from the face and any other external body part.

7. The therapeutic system of claim 6, wherein said treatment additive providing means comprises a means positioned within the vapor chamber, for containing the treatment additive and for exposing the treatment additive directly to the moist heat in vapor form, wherein the treatment additive is absorbed into the moist heat in vapor form.

8. The therapeutic system of claim 6, wherein said generating means further comprises a means positioned within the fluid reservoir for providing a treatment additive directly to the fluid to be vaporized, wherein the treatment additive is incorporated into the moist heat in vapor form.

9. A therapeutic system for applying a moist heat in vapor form to a desired treatment area requiring therapeutic treatment, said system comprising:

means for generating a moist heat in vapor form, said generating means comprising a housing having a vapor chamber and a fluid reservoir, the fluid reservoir receiving a fluid to be vaporized, the housing further having means for heating the fluid received in the fluid reservoir in a first controlled manner to produce moist heat in vapor form, the moist heat in vapor form produced being contained in the vapor chamber, said generating means further comprising a vapor output port and means for providing a treatment additive to the moist heat in vapor form;

interface means remote from said generating means for interfacing the moist heat in vapor form with the desired treatment area and comprising an inner liner and an outer liner, wherein the inner liner comprises a breathable fabric of a first permeability for allowing the moist heat in vapor form therethrough and further for placement in proximity to the desired treatment area, and wherein the outer liner is of a second permeability that is less than the first permeability, whereby the desired treatment area is exposed to the moist heat in vapor form;

delivery means connected between said generating means and said interface means for delivering the moist heat in vapor form from said generating means to said interface means in a second controlled manner wherein said delivery means comprises a pump in connection with the vapor chamber of said generating means for pumping moist heat in vapor form from the vapor chamber through the vapor output port, and wherein said delivery means further comprises a flexible tubing connected between the vapor output port and said interface means for transporting pumped moist heat in vapor form to said interface means; and control means connected with said generating means and said delivery means for controlling the heating of the fluid received in the fluid reservoir in the first controlled manner and further for controlling the delivery of moist heat in vapor form to the treatment area in the second manner, said interfacing, delivery and control means being associatively adapted to selectively apply moist heat in vapor form to any external body part for which treatment is desired.

10. The therapeutic system of claim 9, wherein said interface means further comprises a mask, wherein the mask comprises the inner liner and the outer liner, the mask having a shape in conformity with the desired treatment area.

11. The therapeutic system of claim 9, wherein said interface means further comprises a pad, which pad comprises the inner liner and the outer liner, wherein the inner liner is for placement in intimate contact with the desired treatment area.

12. The therapeutic system of claim 9, wherein said interface means further comprises a tent, which tent comprises the inner liner and the outer liner, the tent providing a controlled atmosphere of the moist heat in vapor form around the desired treatment area.

13. The therapeutic system of claim 9, wherein said treatment additive providing means comprises a means positioned within the vapor chamber, for containing the treatment additive and for exposing the treatment additive directly to the moist heat in vapor form, wherein the treatment additive is absorbed into the moist heat in vapor form.

14. The therapeutic system of claim 9, wherein said generating means further comprises a means positioned within the fluid reservoir for providing a treatment additive directly to the fluid to be vaporized, wherein the treatment additive is incorporated into the moist heat in vapor form.

15. A therapeutic system for applying a moist heat in vapor form to a desired treatment area requiring therapeutic treatment, said system comprising:

means for generating a moist heat in vapor form, said generating means comprising a housing having a vapor chamber and a fluid reservoir, the fluid reservoir receiving a fluid to be vaporized, the housing further having means for heating the fluid received in the fluid reservoir in a first controlled manner to produce moist heat in vapor form, the moist heat in vapor form produced being contained in the vapor chamber, said generating means further comprising a vapor output port and means for providing a treatment additive to the moist heat in vapor form;

interface means remote from said generating means for interfacing the moist heat in vapor form with the desired treatment area and comprising an inner liner and an outer liner, wherein the inner liner comprises a breathable fabric of a first permeability for allowing the moist heat in vapor form therethrough and further for placement in proximity to the desired treatment area, and wherein the outer liner is of a second permeability that is less than the first permeability to effectively prevent the moist heat in vapor form from escaping therethrough, whereby the desired treatment area is exposed to the moist heat in vapor form;

delivery means connected between said generating means and said interface means for delivering the moist heat in vapor form from said generating means to said interface means in a second controlled manner wherein said delivery means comprises a pump in connection with the vapor chamber of said generating means for pumping moist heat in vapor form from the vapor chamber through the vapor output port, and wherein said delivery means further comprises a flexible tubing connected between the vapor output port and said interface means for transporting pumped moist heat in vapor form to said interface means; and control means connected with said generating means and said delivery means for controlling the heating of the fluid received in the fluid reservoir in the first controlled manner and further for controlling the delivery of moist heat in vapor form to the treatment area in the second manner, said interfacing, delivery and control means being associatively adapted to selectively apply moist heat in vapor form to any external body part for which treatment is desired.

\* \* \* \* \*